(12) United States Patent
Shah et al.

(10) Patent No.: US 8,740,845 B2
(45) Date of Patent: *Jun. 3, 2014

(54) MULTI-LAYER FILM WELDED ARTICULATED BALLOON

(75) Inventors: Tilak M. Shah, Cary, NC (US); Christopher D. Strom, Cary, NC (US)

(73) Assignee: Polyzen Inc., Apex, NC (US)

(*) Notice: Subject to any disclaimer, the term of this patent is extended or adjusted under 35 U.S.C. 154(b) by 94 days.

This patent is subject to a terminal disclaimer.

(21) Appl. No.: 13/154,229

(22) Filed: Jun. 6, 2011

(65) Prior Publication Data

US 2011/0295202 A1    Dec. 1, 2011

Related U.S. Application Data

(63) Continuation of application No. 12/237,897, filed on Sep. 25, 2008, now Pat. No. 7,976,497.

(60) Provisional application No. 60/974,884, filed on Sep. 25, 2007.

(51) Int. Cl.
*A61M 37/00* (2006.01)
*A61M 31/00* (2006.01)
*A61M 29/00* (2006.01)

(52) U.S. Cl.
USPC .................................. 604/103.06; 604/96.01

(58) Field of Classification Search
USPC ............ 604/103.06, 96.01, 194, 101.02, 103, 604/103.01–103.08, 103.11–103.14
See application file for complete search history.

(56) References Cited

U.S. PATENT DOCUMENTS

| | | | |
|---|---|---|---|
| 2,703,770 | A | 3/1955 | Melzer |
| 3,164,151 | A | 1/1965 | Nicoll |
| 4,043,345 | A | 8/1977 | Kramann et al. |
| 4,311,146 | A | 1/1982 | Wonder |
| 4,327,736 | A | 5/1982 | Inoue |
| 4,483,030 | A | 11/1984 | Flick et al. |
| 4,555,242 | A | 11/1985 | Saudagar |
| 4,650,463 | A | 3/1987 | LeVeen et al. |
| 4,784,133 | A | 11/1988 | Mackin |

(Continued)

FOREIGN PATENT DOCUMENTS

| | | | |
|---|---|---|---|
| JP | 51-090376 A | 8/1976 |
| JP | 51-100833 A | 9/1976 |

(Continued)

OTHER PUBLICATIONS

Unpublished U.S. Appl. No. 11/933,018, filed Oct. 31, 2007.

(Continued)

*Primary Examiner* — Nicholas Lucchesi
*Assistant Examiner* — Pritesh Patel
(74) *Attorney, Agent, or Firm* — Hultquist, PLLC; Steven J. Hultquist

(57) ABSTRACT

A method of fabrication of a medical balloon, and a balloon device useful for various medical balloon procedures, such as gastrointestinal, vascular, reproductive system, urinary system and pulmonary applications. At least two layers of a thermoplastic film are sealed at their peripheral edges and heat sealed at one or more locations inside an area enclosed by the sealed edges at predetermined locations, in one implementation of the balloon device. Such configuration enables the balloon to articulate to a desired shape upon inflation, with the desired shape being selected to accommodate a specific medical application.

21 Claims, 5 Drawing Sheets

(56) References Cited

U.S. PATENT DOCUMENTS

| | | |
|---|---|---|
| 4,994,033 A | 2/1991 | Shockey |
| 5,022,109 A | 6/1991 | Pekar |
| 5,116,310 A | 5/1992 | Seder et al. |
| 5,219,792 A | 6/1993 | Kim et al. |
| 5,234,454 A | 8/1993 | Bangs |
| 5,304,135 A | 4/1994 | Shonk |
| 5,309,896 A | 5/1994 | Moll et al. |
| 5,355,087 A | 10/1994 | Claiborne et al. |
| 5,360,414 A | 11/1994 | Yarger |
| 5,433,252 A | 7/1995 | Wolf et al. |
| 5,451,232 A | 9/1995 | Rhinehart et al. |
| 5,512,051 A | 4/1996 | Wang et al. |
| 5,527,280 A | 6/1996 | Goelz |
| 5,545,122 A | 8/1996 | Spruill |
| 5,545,220 A | 8/1996 | Andrews et al. |
| 5,598,593 A | 2/1997 | Wolfe |
| 5,679,423 A | 10/1997 | Shah |
| 5,704,913 A | 1/1998 | Abele et al. |
| 5,716,329 A | 2/1998 | Dieter |
| 5,743,852 A | 4/1998 | Johnson |
| 5,776,159 A | 7/1998 | Young |
| 5,782,800 A | 7/1998 | Yoon |
| 5,833,915 A | 11/1998 | Shah |
| 5,843,116 A | 12/1998 | Crocker et al. |
| 5,855,588 A | 1/1999 | Young |
| 5,865,729 A | 2/1999 | Meehan et al. |
| 5,868,776 A | 2/1999 | Wright |
| 5,879,499 A | 3/1999 | Corvi |
| 5,924,456 A | 7/1999 | Simon |
| 5,935,115 A | 8/1999 | Espina |
| 5,951,514 A | 9/1999 | Sahota |
| 5,996,639 A | 12/1999 | Gans et al. |
| 6,015,382 A | 1/2000 | Zwart et al. |
| 6,022,313 A | 2/2000 | Ginn et al. |
| 6,066,154 A | 5/2000 | Reiley et al. |
| 6,102,929 A | 8/2000 | Conway et al. |
| 6,156,053 A | 12/2000 | Ghandi et al. |
| 6,217,548 B1 | 4/2001 | Tsugita et al. |
| 6,249,708 B1 | 6/2001 | Nelson et al. |
| 6,291,543 B1 | 9/2001 | Shah |
| 6,352,077 B1 | 3/2002 | Shah |
| 6,371,910 B1 | 4/2002 | Zwart et al. |
| 6,409,741 B1 | 6/2002 | Crocker |
| 6,460,541 B1 | 10/2002 | Shah et al. |
| 6,478,789 B1 | 11/2002 | Spehalski et al. |
| 6,510,574 B2 | 1/2003 | Sharrock et al. |
| 6,520,977 B2 | 2/2003 | Piraka |
| 6,663,646 B1 | 12/2003 | Shah |
| 6,712,832 B2 | 3/2004 | Shah |
| 6,733,512 B2 | 5/2004 | McGhan |
| 6,746,465 B2 | 6/2004 | Diederich et al. |
| 6,805,662 B2 | 10/2004 | Shah et al. |
| 6,827,710 B1 | 12/2004 | Mooney et al. |
| 6,875,193 B1 | 4/2005 | Bonnette et al. |
| 6,981,980 B2 | 1/2006 | Sampson et al. |
| 7,041,056 B2 | 5/2006 | Deslauriers et al. |
| 7,112,186 B2 | 9/2006 | Shah |
| 7,470,251 B2 | 12/2008 | Shah |
| 7,976,497 B2 * | 7/2011 | Shah et al. ............ 604/103.06 |
| 2001/0011174 A1 | 8/2001 | Reiley et al. |
| 2003/0028097 A1 | 2/2003 | D'Amico et al. |
| 2003/0028211 A1 | 2/2003 | Crocker et al. |
| 2003/0088209 A1 | 5/2003 | Chiu et al. |
| 2005/0015047 A1 | 1/2005 | Shah |
| 2005/0222329 A1 | 10/2005 | Shah |
| 2006/0212064 A1 | 9/2006 | Shah |
| 2007/0212559 A1 | 9/2007 | Shah |
| 2007/0239110 A1 | 10/2007 | Shah |
| 2007/0299463 A1 | 12/2007 | Shah |
| 2008/0086083 A1 | 4/2008 | Towler |
| 2008/0172080 A1 | 7/2008 | Isham |
| 2008/0188802 A1 | 8/2008 | Shah |
| 2008/0262449 A1 | 10/2008 | Shah |
| 2008/0262450 A1 | 10/2008 | Shah |
| 2009/0082724 A1 | 3/2009 | Shah et al. |
| 2010/0137797 A2 | 6/2010 | Shah et al. |

FOREIGN PATENT DOCUMENTS

| | | |
|---|---|---|
| JP | 51-101084 A | 9/1976 |
| JP | 10-127771 A | 5/1998 |
| WO | 9814123 A1 | 4/1998 |
| WO | 9920321 A2 | 4/1999 |

OTHER PUBLICATIONS

Civil Action No. 5:11-CV-0062-D, U.S. District Court for the Eastern District of North Carolina, Western Division; filed Nov. 21, 2011; pending litigation.

Civil Action No. 5:12-CV-00102-D, U.S. District Court for the Eastern District of North Carolina, Western Division; filed Dec. 23, 2011; litigation proceedings consolidated with Civil Action No. 5:11-CV-0062-D by order on Jul. 2, 2012.

"Polyzen Corrected Opposition to Radiadyne Combined Motion to Dismiss and to Correct Inventorship Filed on Jan. 24, 2012 in U.S. Dist. Court East. Dist. of NC West. Div. Case No. 5:11-cv-00662-D, including Exhibits A-L and Affidavits", pp. 1-24, No. 17.

"Radiadyne Reply in Support of Its Combined Motion to Dismiss Under Rule 12(B)(1) and to Correct Inventorship Filed on Jan. 27, 2012 in U.S. Dist. Court East. Dist. of NC West. Div. Case No. 5:11-cv-00662-D, without exhibits", pp. 1-11, No. 19.

"Polyzen and Radiadyne Joint Claim Construction Statement Filed on Apr. 12, 2013 in U.S. Dist. Court East. Dist. of NC West. Div. Case No. 5:11-cv-00662-D, including Claim Construction Chart Exhibit", pp. 1-17, No. 41.

"Plaintiff Polyzen Opening Brief on Claim Construction Filed on Apr. 30, 2013 in U.S. Dist. Court East. Dist. of NC West. Div. Case No. 5:11-cv-00662-D, including Exhibits A-U", pp. 1-254, No. 55.

"Radiadyne Opening Claim Construction Brief Filed on Apr. 30, 2013 in U.S. Dist. Court East. Dist. of NC West. Div. Case No. 5:11-cv-00662-D, including Declaration T. Morrow with Exhibits A-G", pp. 1-103, No. 54.

"Polyzen Responsive Claim Construction Brief Filed on May 21, 2013 in U.S. Dist. Court East. Dist. of NC West. Div. Case No. 5:11-cv-00662-D", pp. 1-11, No. 63.

"Radiadyne Responsive Claim Construction Brief Filed on May 21, 2013 in U.S. Dist. Court East. Dist. of NC West. Div. Case No. 5:11-cv-00662-D, including Exhibit", pp. 1-36, No. 62.

"Answer and Affirmative Defenses of Defendant Polyzen Filed on May 31, 2012 in U.S. Dist. Court East. Dist. of NC West. Div. Case No. 5:12-cv-00102-D", pp. 1-9, No. 23.

"Polyzen Reply Claim Construction Brief Filed on May 31, 2013 in U.S. Dist. Court East. Dist. of NC West. Div. Case No. 5:11-cv-00662-D, including Exhibit", pp. 1-21, No. 64.

"Polyzen Cross Motion for Summary Judgment on Radiadyne Affirmative Defense of Co-Inventorship Filed on Jun. 28, 2013 in U.S. Dist. Court East. Dist. of NC West. Div. Case No. 5:11-cv-00662-D", pp. 1-3, No. 72.

"Polyzen Memo. of Law in Opposition to Radiadyne Motion for Summary Judgment of Co-Inventorship and in Support Cross Motion Filed on Jun. 28, 2013 in U.S. Dist. Court East. Dist. of NC West. Div. Case No. 5:11-cv-00662-D, including Exhibits A-M", pp. 1-93, No. 73.

"Answer of Defendant and Counter-Plaintiff Radiadyne Filed on Oct. 1, 2012 in U.S. Dist. Court East. Dist. of NC West. Div. Case No. 5:11-cv-00662-D", pp. 1-8, No. 32.

"Order Issued on Oct. 31, 2013 in U.S. Dist. Court East. Dist. of NC West. Div. Case No. 5:11-cv-00662-D", pp. 1-2, No. 88.

"Polyzen First Amended Complaint Filed on Nov. 4, 2013 in U.S. Dist. Court East. Dist. of NC West. Div. Case No. 5:11-cv-00662-D", pp. 1-16, No. 89.

"Answer of Defendant and Counter-Plaintiff Radiadyne to Polyzen First Amended Complaint Filed on Nov. 18, 2013 in U.S. Dist. Court

(56) References Cited

OTHER PUBLICATIONS

East. Dist. of NC West. Div. Case No. 5:11-cv-00662-D", pp. 1-29, No. 91.
"Polyzen Complaint Against Radiadyne Filed on Nov. 21, 2011 in U.S. Dist. Court East. Dist. of NC West. Div. Case No. 5:11-cv-00662-D, including Exhibits A, B, and C", pp. 1-22, No. 1.
"Radiadyne Motion to Dismiss and Correct Inventorship Filed on Dec. 13, 2011 in U.S. Dist. Court East. Dist. of NC West. Div. Case No. 5:11-cv-00662-D, including Exhibits A, B, C, D, and F", pp. 1-48, No. 10.
"Radiadyne Complaint Filed on Dec. 23, 2011 in U.S. Dist. Court East. Dist. of NC West. Div. Case No. 5:12-cv-00102-D", pp. 1-14, No. 1.

* cited by examiner

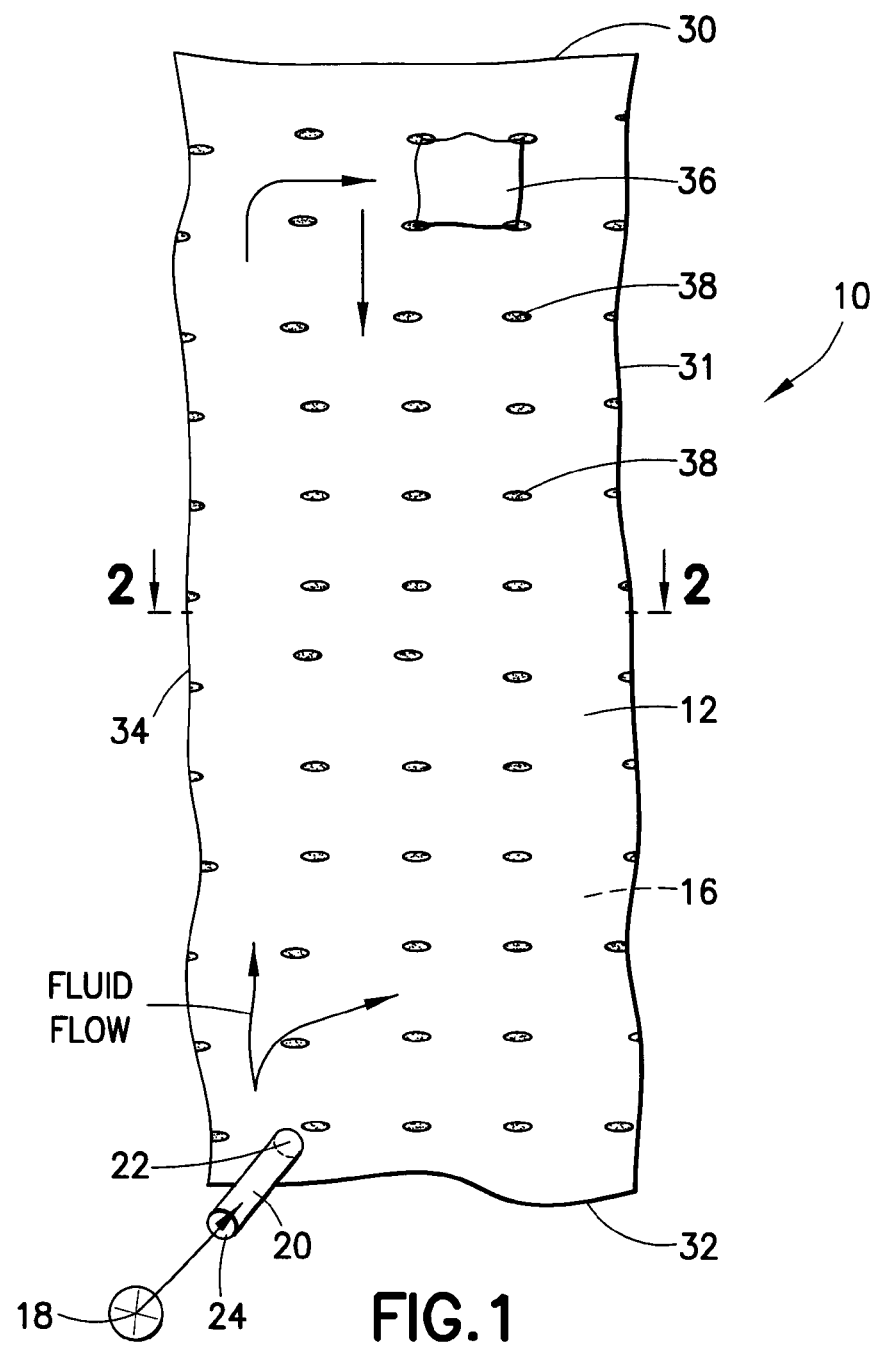
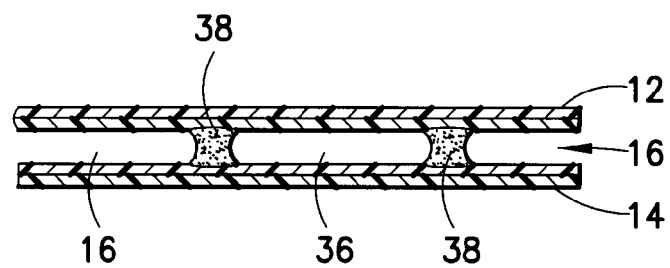

MULTI-LAYER FILM WELDED ARTICULATED BALLOON

CROSS-REFERENCE TO RELATED APPLICATIONS

This application is a continuation under 35 U.S.C. §120 of U.S. patent application Ser. No. 12/237,897 filed Sep. 25, 2008 in the names of TILAK M. SHAH and CHRISTOPHER D. STROM for "Multi-Layer Film Welded Articulated Balloon," issued on Jul. 12, 2011 as U.S. Pat. No. 7,976,497, which in turn claims the benefit of priority under 35 U.S.C. §119 of U.S. Provisional Patent Application No. 60/974,884 filed Sep. 25, 2007 in the names of TILAK M. SHAH and CHRISTOPHER D. STROM for "Multi-Layer Film Welded Articulated Balloon." The disclosure of U.S. Provisional Patent Application No. 60/974,884 and U.S. patent application Ser. No. 12/237,897 are hereby incorporated herein by reference, in their respective entireties for all purposes.

BACKGROUND OF THE INVENTION

1. Field of the Invention

The present invention relates to low pressure medical balloon articles and to the methodology for making the same, and in particular to a medical balloon useful for in vivo luminal medical procedures.

2. Description of the Prior Art

Various balloon articles are in use for cardiovascular and other medical procedures (such as percutaneous transluminal angioplasty, percutaneous transluminal nephrostomy, urethral dilatation, biliary duct dilatation, percutaneous transluminal renal angioplasty, and the like). Balloons may be utilized for such procedures, that are inflatable or otherwise capable of holding pressure. Pressure levels of balloons may be widely varied, depending on the specific application, and may for example be in a range of from 30-150 pounds per square inch (psi) for higher pressures and balloons and 1-10 psi for low pressure balloons.

Low pressure balloons are there which can hold a pressure on the order of 1-3 psi. Low pressure balloons are typically used for gastrointestinal applications. In other applications, balloons are employed in cardiovascular applications for blocking blood flow, or for removing/blocking a blood clot. In such applications, the balloon is typically bonded to the shaft of a catheter, and after inflation and use, the balloon is readily retracted to an original catheter sleeve shape.

An issue confronting the use of balloon articles for in vivo usage is the asymmetric character of the inflation.

There have been various attempts to shape the balloon so it can be articulated after inflation in vivo for its intended use. For example, in angioplasty applications, clots found in arteries should be held against the artery walls until treated or removed. In prostate treatments it is often desirable to space the prostate from the rectum while treating the same with radiation.

Usually, to achieve the desired inflated shape in low pressure balloons, the balloon material, often latex, is pre-stretched so as to achieve the desired final shape or the balloon has discrete portions which are overinflated so as to assume a desired shape after insertion and inflation. Another tactic employed is to precure particular selected balloon material so that when inflated, the balloon will assume the precured shape, or to form the balloon with a wall thickness which may vary at different locations in the balloon so as to expand at different rates to achieve different shaped portions in the balloon.

While the resultant balloon would be operational for its intended purpose, each requires an involved fabrication methodology.

SUMMARY OF THE INVENTION

The present invention relates to balloon articles useful in various medical procedures.

In one aspect, the present invention provides a method of fabrication of a medical balloon which uses at least two layers of a thermoplastic film sealed at their edges or periphery and heat sealed at one or more locations inside the area enclosed by the sealed edge at preselected locations, which enables the balloon to articulate to a desired shape upon inflation, with the specific shape being dependent on the particular medical application. The layers may have a different thickness or modulus of elasticity or any combination thereof or the same thickness and modulus, and different dimensioned channels formed by the heat sealed locations to articulate to a desired shape.

In a specific aspect, the invention relates to a method for the fabrication of an articulated medical balloon device comprising the steps of:

(a) providing at least two film layers having opposed edges;

(b) sealing said opposed edges to form a compartment adapted to receive fluid to expand said film layers relative to each other;

(c) providing an opening in said fluid compartment that is adapted to receive a lumen; and (d) forming a subcompartment between the sealed edges of said compartment of a predetermined shape and dimension by sealing at least one of said layers to another, intermediate said opposed edges.

In a further aspect, the invention relates to a medical balloon device, comprising:

at least one film layer having an edge secured to a second film layer to form a fluid compartment therebetween, and portions of said film layers between said edges being secured intermediate said edges to form a plurality of subcompartments, and said fluid compartment being provided with an opening to receive a lumen.

Additional aspects, features and embodiments will be more fully apparent from the ensuing disclosure and appended claims.

BRIEF DESCRIPTION OF THE DRAWINGS

FIG. 1 is a top plan view of one embodiment of the balloon of the present invention.

FIG. 2 is a cross-sectional view of the balloon of FIG. 1 taken substantially along the plane indicated by the line 2-2 of FIG. 1.

DETAILED DESCRIPTION OF THE PREFERRED EMBODIMENTS

Figure 3:
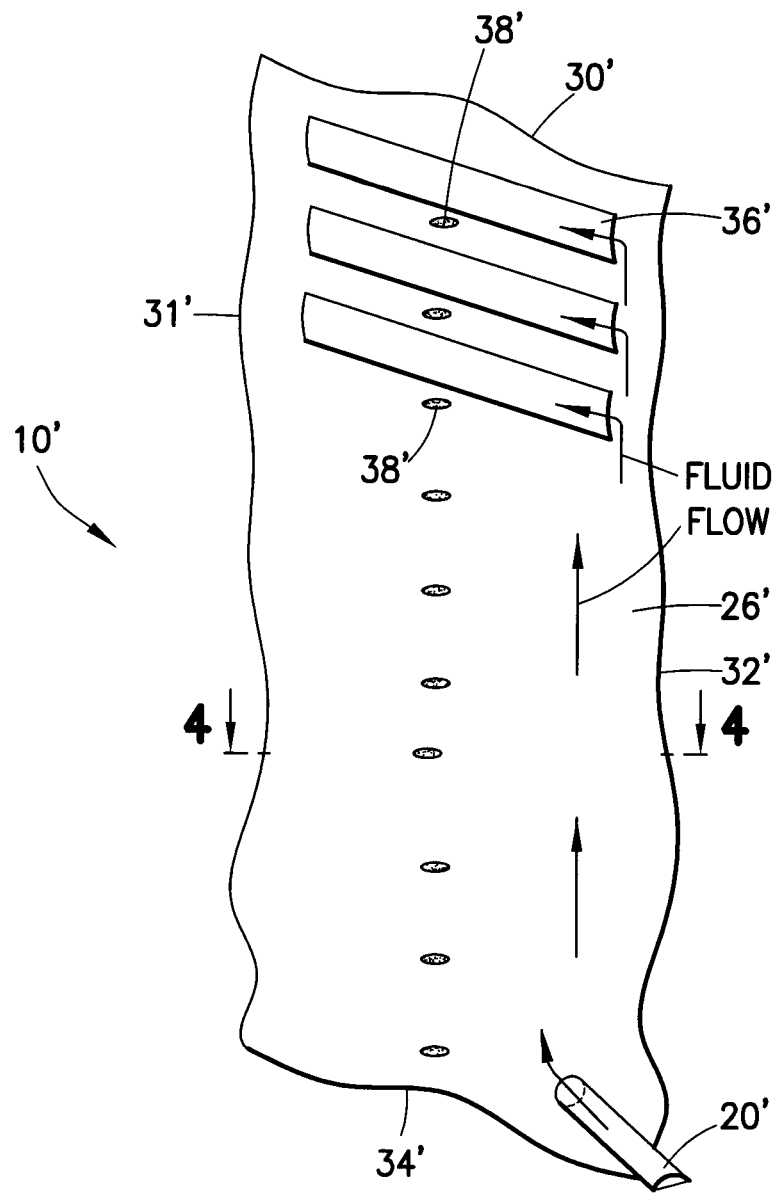
FIG. 3 is a top plan view of a second embodiment of the balloon of the present invention.

Referring now to the drawings in detail, wherein like numerals indicate like elements throughout the several views, each of the inflatable balloon structures of the present invention, e.g., the balloon structure 10 of FIG. 1, comprises a multilayer arrangement of film layers 12, 14 or more, that includes an inflatable compartment 16 defining an enclosed interior volume and an anti-reflux valve 18 positioned in a lumen or fluid passage 20 whose distal end 22 is sealingly connected to the interior volume of compartment 16. An inflation bulb 24 is connected to the proximal end 24 of lumen 20 upstream from the anti-reflux valve 18. The valve 18 may be a one-way check valve or a rotatable stem in a housing having an opening adapted to be rotated into alignment with the bore of the lumen 20.

Oppositely facing film layers 26, 28 are bonded to one another along their edges 30-31, 32 and 34 to form the inflatable compartment 16 and the compartment 16 is divided into subcompartments 36 by tack or spot welds 38 so that the subcompartments 36 are virtually square-shaped in plan so that upon inflation, the balloon compartment 16 will resemble a tufted cushion with the tack or spot welds 38 forming raised square-shaped subcompartments. This device can be used to separate two organs in the body in vivo and support the same in spaced relation.

The inflatable balloon compartment and subcompartments can be readily formed by heat-sealing or other joining techniques commonly known and used in the art for forming structural articles from thermoplastic film materials in the form of web or sheet stock. For example, RF welding, heat impulse welding, solvent welding, adhesive bonding and the like can be employed.

Figure 4:
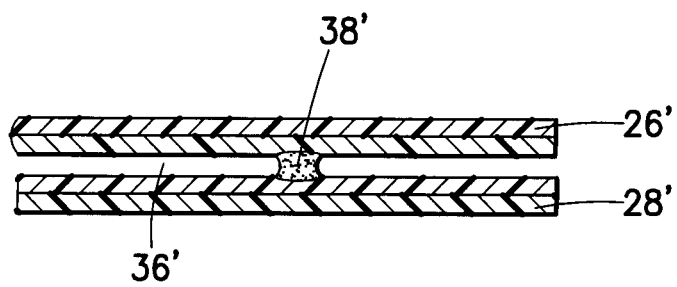
FIG. 4 is a cross-sectional view of the balloon of FIG. 3 taken substantially along the plane indicated by the line 4-4 of FIG. 3.
Figure 5:
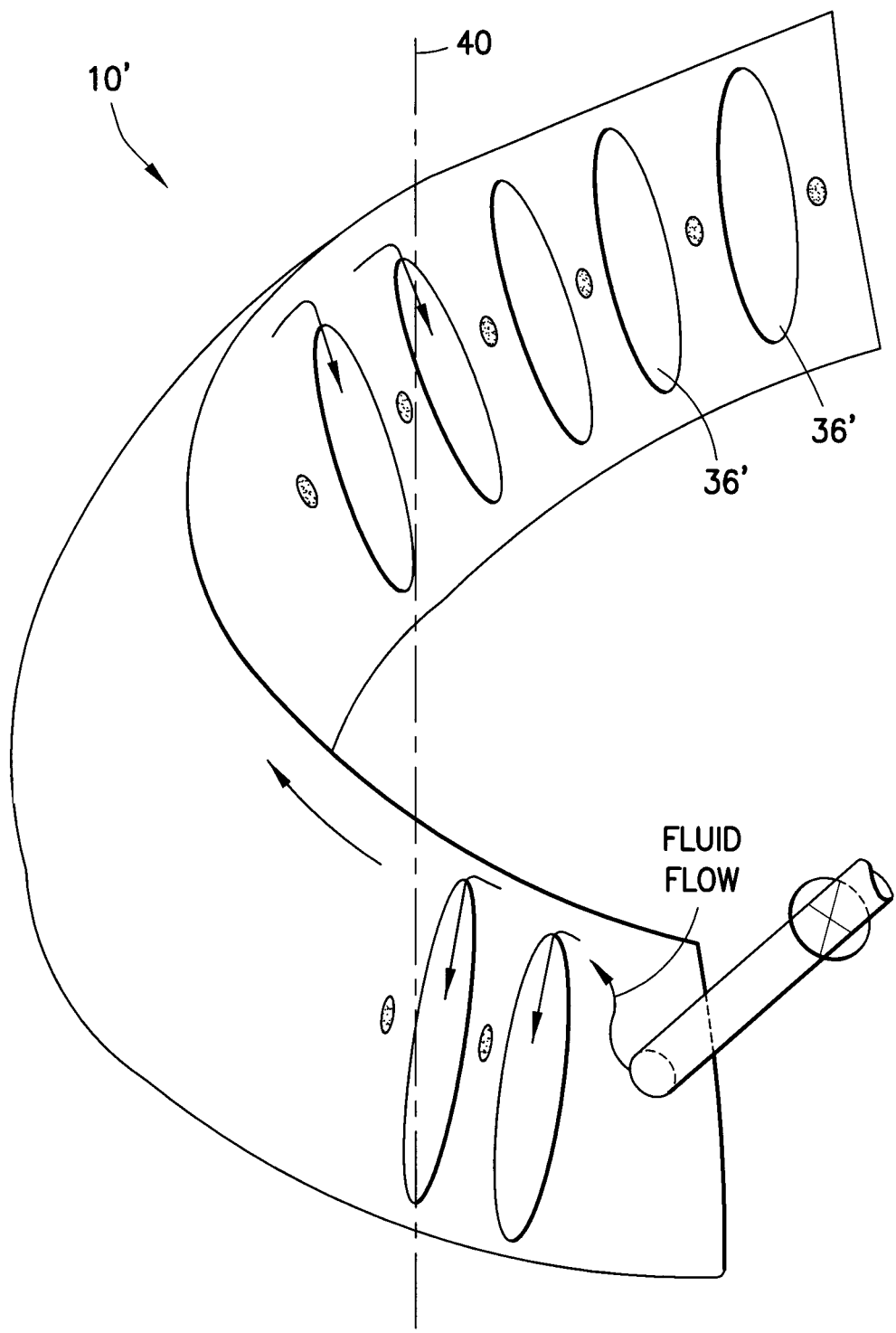
FIG. 5 is a perspective view of the articulated balloon of FIG. 3 after inflation.

Referring to the embodiment of the invention illustrated in FIGS. 3 to 5, inclusive, the film layers 26' and 28' may be bonded to each other in the shape of a parallelogram, with subcompartments 36" extending in spaced relation to each other, but parallel to the side edges 30' and 34' and at an angle to the opposite edges 31' and 32' by tack or spot welds 38'. As shown in FIG. 5, upon inflation, the fluid force introduced into the subcompartments 36' will cause the balloon device 10' to curl into a spiral about a longitudinal axis 40.

Figure 6:
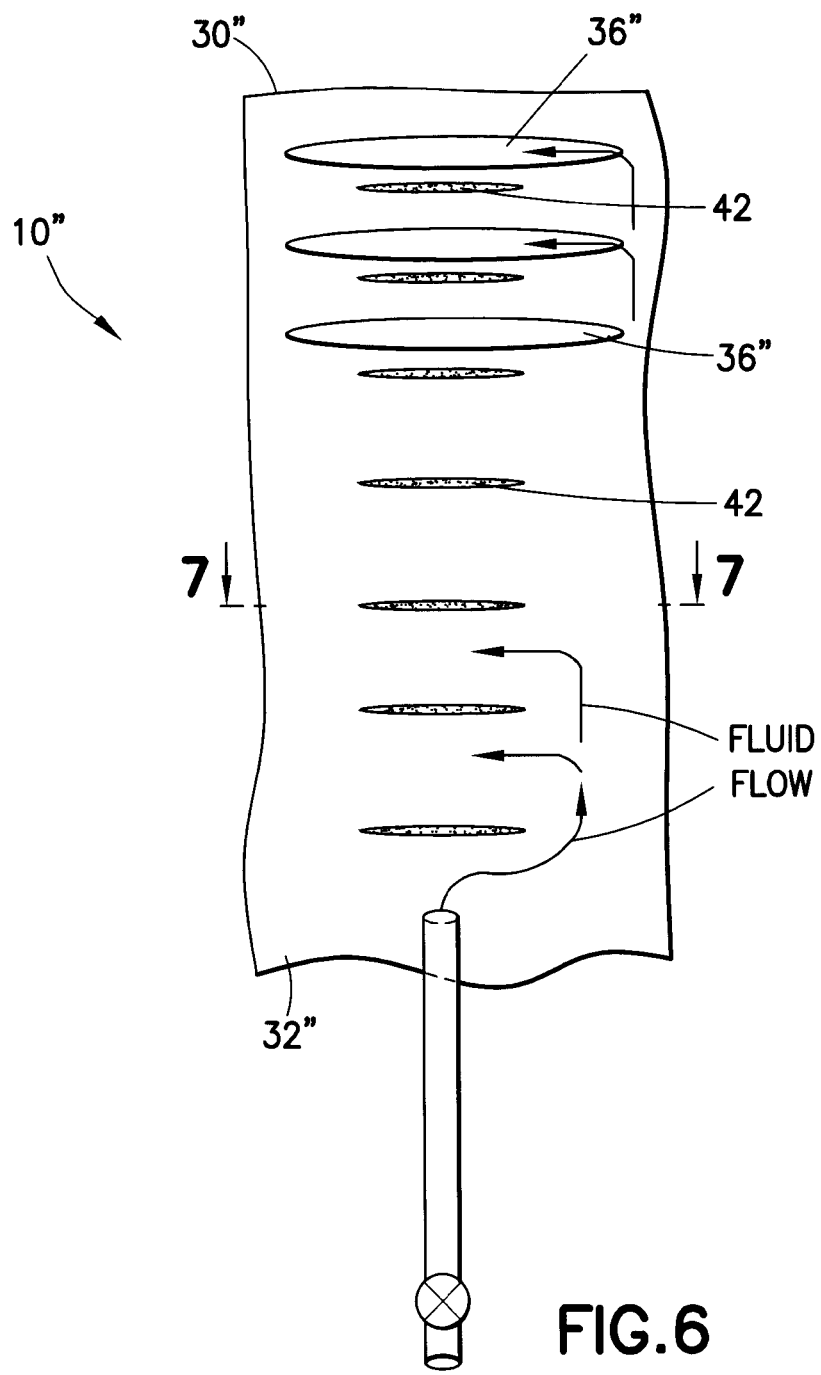
FIG. 6 is a top plan view of yet another embodiment of the balloon of the present invention.
Figure 7:
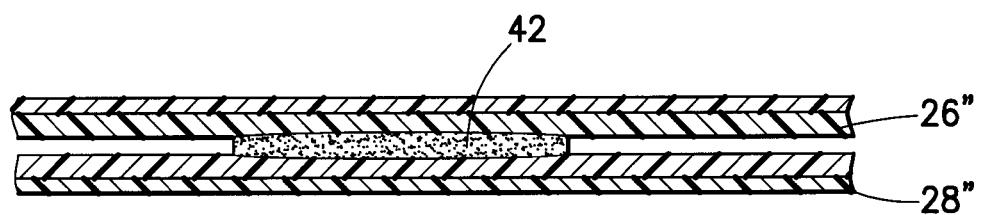
FIG. 7 is a cross-sectional view of the balloon of FIG. 6 taken substantially along the plane indicated by line 7-7 of FIG. 6.

Referring to FIGS. 6 and 7, the balloon device 10" can be formed with rectangular subcompartments 36" utilizing line welds 42, parallel to edges 30" and 32".

Figure 8:
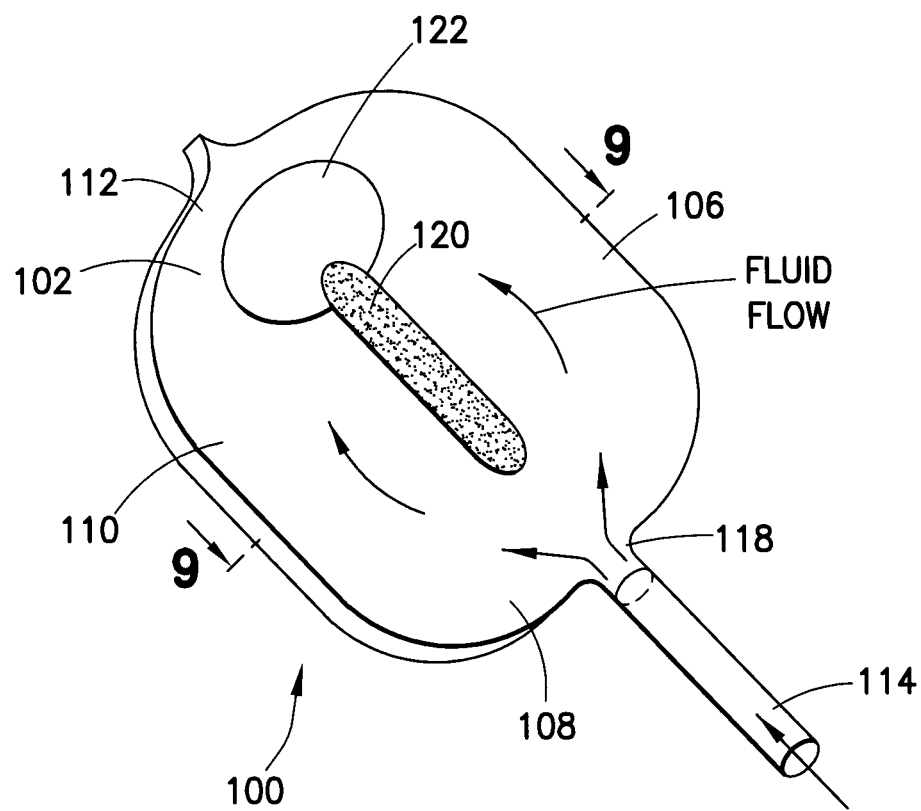
FIG. 8 is a perspective view of still another embodiment of an articulated balloon according to the present invention.
Figure 9:
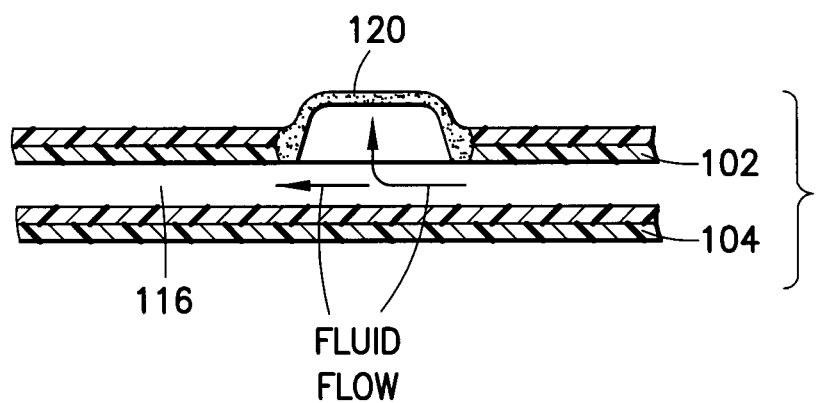
FIG. 9 is a cross-sectional view of the balloon of FIG. 8 taken substantially along the plane indicated by line 9-9 of FIG. 8.

As shown in the embodiment illustrated in FIGS. 8 and 9, the balloon device 100 has thermoplastic film layers 102 and 104 having different properties joined along their edges 106, 108, 110, and 112. For example, the materials can have a different modulus of elasticity, meaning that they will stretch under pressure at different rates to form a particular arcuate or curved shape. In this embodiment, the lumen 114 can extend into the interior of the compartment 116 formed by the film layers 102 and 104 and sealed to the balloon at neck 118.

Additionally, a third layer or strip of film 120 can be added or joined to the top layer 102 to increase its thickness. This will cause the sides 108, 112 to be drawn inwardly relative to the lumen axis, upon inflation, while the distal or forward portion of the compartment 122 will bulge upwardly. Such a device is useful in prostate surgery to support the prostate in spaced relation to other organs.

It will therefore be appreciated that the medical balloon device of the invention may be widely varied in construction and features. In one embodiment, the balloon device includes at least one neck member in a sealing area of the device. The device in a further embodiment comprises at least one area outside of the secured edges forming an inflation port.

While the invention has been illustratively shown and described with respective to particular embodiments, it will be appreciated that the application is not thus limited, but rather extends to and encompasses other variations, modifications and additional embodiments as will be apparent to those of ordinary skill in the art, based on the disclosure herein. Accordingly, the invention is intended to be broadly construed with respect to the ensuing claims, as encompassing all such additional variations, modifications and alternative embodiments.

What is claimed is:

1. A medical balloon device, comprising a multiplicity of layers of thermoplastic film including layers sealed at peripheral edges thereof to form an inflatable interior volume enclosed by the sealed edges, and layers sealed at one or more locations in the interior volume to enable the device to articulate to a predetermined shape upon inflation of the interior volume with an inflation fluid, to accommodate a predetermined medical application, wherein the inflatable interior volume is adapted to receive an inflation fluid.

2. The medical balloon device of claim 1, wherein the layers sealed at one or more locations in the interior volume to enable the device to articulate to a predetermined shape upon inflation of the interior volume with an inflation fluid, have a different modulus of elasticity.

3. The medical balloon device of claim 1, wherein the layers sealed at one or more locations in the interior volume to enable the device to articulate to a predetermined shape upon inflation of the interior volume with an inflation fluid, have a different thickness.

4. The medical balloon device of claim 1, comprising two layers of thermoplastic film.

5. The medical balloon device of claim 1, comprising three layers of thermoplastic film.

6. The medical balloon device of claim 1, comprising a layer forming a compartment that is exterior to said interior volume.

7. The medical balloon device according to claim 1, wherein said predetermined shape accommodates a predetermined medical application selected from the group consisting of gastrointestinal, vascular, reproductive system, urinary system and pulmonary applications.

8. The medical balloon device according to claim 1, wherein said predetermined shape accommodates a prostatic medical application.

9. The medical balloon device according to claim 1, wherein one of said layers is an intermediate layer in said interior volume configured to form compartments, one of which is an inflation compartment adapted for coupling with a luminal element to enable inflation of the interior volume and another one of which bulges outwardly upon inflation so that the device articulates to said predetermined shape.

10. A medical balloon device, comprising:
a first thermoplastic film layer including a first edge;
a second thermoplastic film layer including a second edge joined to the first edge to form a bottom inflatable compartment between the first and second layer;
a third thermoplastic film layer including a third edge joined to the second edge to form a top inflatable compartment between the second and third layer, in fluid communication with the bottom inflatable compartment; and said bottom inflatable compartment being adapted to receive an inflation fluid and said top inflatable compartment being adapted to articulate to a predetermined shape to accommodate a predetermined medical application.

11. The medical balloon device of claim 10, wherein the second and third layers are secured intermediate said second and third edges so that the distal portion of the third layer bulges upwardly upon inflation.

12. The medical balloon device of claim 10, wherein the top inflatable compartment is adapted to distend to form a bulged conformation of the distal portion of the third layer relative to the proximal portion upon inflation.

13. The medical balloon device of claim 10, wherein the top inflatable compartment is further secured between the second and third layers intermediate said second and third edges to form an arcuate shape in the distal portion of the third layer upon inflation.

14. The medical balloon device of claim 10, wherein the second and third layers are secured at an intermediate portion so that said third layer upon inflation bulges upwardly between the intermediate portion and the third edge at the distal portion of the third layer.

15. A medical balloon device, comprising a balloon body including at least two layers of thermoplastic film sealed at peripheral edges thereof and sealed at one or more locations inside an area enclosed by the sealed edges at predetermined locations, wherein an additional layer of thermoplastic film of said balloon body is disposed in relation to said at least two layers of thermoplastic film to form compartments in an interior volume of said balloon body including a first compartment adapted to receive an inflation fluid, and a second compartment communicating with said first compartment and configured to enable the balloon body to articulate to a predetermined shape upon inflation with said inflation fluid to accommodate a predetermined medical application.

16. The medical balloon device according to claim 15, wherein said predetermined shape accommodates a predetermined medical application selected from the group consisting of gastrointestinal, vascular, reproductive system, urinary system and pulmonary applications.

17. The medical balloon device according to claim 15, wherein said predetermined shape accommodates a prostatic medical application.

18. The medical balloon device according to claim 15, wherein said at least two layers and said additional layer of thermoplastic film comprise polyurethane thermoplastic film.

19. The medical balloon device according to claim 15, wherein said at least two layers and said additional layer of thermoplastic film comprise at least two layers of differing modulus of elasticity to enable such layers to distend at different rates during said inflation with said inflation fluid, to form a predetermined arcuate or curved shape.

20. The medical balloon device according to claim 15, further comprising a luminal element coupled to said first compartment to enable inflation of the balloon body with said inflation fluid.

21. The medical balloon device according to claim 20, further comprising a source of inflation gas coupled to a proximal end of said luminal element, with a distal end of said luminal element coupled to said first compartment.

* * * * *

(12) EX PARTE REEXAMINATION CERTIFICATE (10347th)
United States Patent
Shah et al.

(10) Number: US 8,740,845 C1
(45) Certificate Issued: *Oct. 20, 2014

(54) MULTI-LAYER FILM WELDED ARTICULATED BALLOON

(75) Inventors: Tilak M. Shah, Cary, NC (US); Christopher D. Strom, Cary, NC (US)

(73) Assignee: Polyzen Inc., Apex, NC (US)

Reexamination Request:
No. 90/013,258, Jul. 8, 2014

Reexamination Certificate for:
Patent No.: 8,740,845
Issued: Jun. 3, 2014
Appl. No.: 13/154,229
Filed: Jun. 6, 2011

(*) Notice: This patent is subject to a terminal disclaimer.

Related U.S. Application Data

(63) Continuation of application No. 12/237,897, filed on Sep. 25, 2008, now Pat. No. 7,976,497.

(60) Provisional application No. 60/974,884, filed on Sep. 25, 2007.

(51) Int. Cl.
*A61M 37/00* (2006.01)
*A61M 31/00* (2006.01)
*A61M 29/00* (2006.01)

(52) U.S. Cl.
USPC .................................. 604/103.06; 604/96.01

(58) Field of Classification Search
None
See application file for complete search history.

(56) References Cited

To view the complete listing of prior art documents cited during the proceeding for Reexamination Control Number 90/013,258, please refer to the USPTO's public Patent Application Information Retrieval (PAIR) system under the Display References tab.

*Primary Examiner* — William Doerrler

(57) ABSTRACT

A method of fabrication of a medical balloon, and a balloon device useful for various medical balloon procedures, such as gastrointestinal, vascular, reproductive system, urinary system and pulmonary applications. At least two layers of a thermoplastic film are sealed at their peripheral edges and heat sealed at one or more locations inside an area enclosed by the sealed edges at predetermined locations, in one implementation of the balloon device. Such configuration enables the balloon to articulate to a desired shape upon inflation, with the desired shape being selected to accommodate a specific medical application.

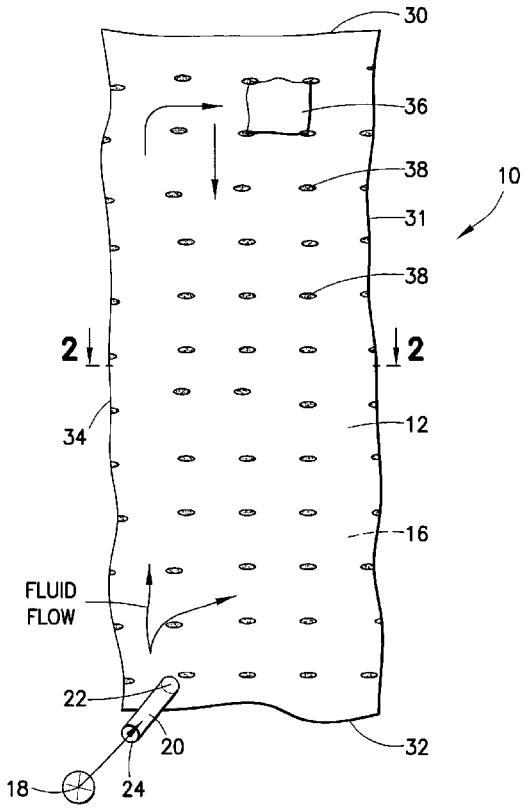

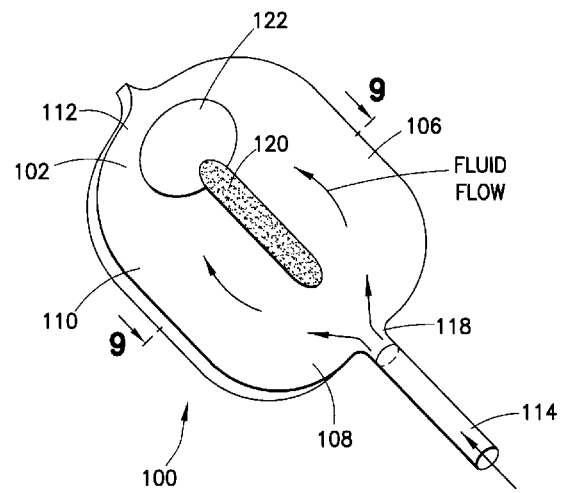

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claims 10, 15, 18, 20 and 21 is confirmed.

Claim 1 is determined to be patentable as amended.

Claims 3-5 and 7, dependent on an amended claim, are determined to be patentable.

Claims 2, 6, 8, 9, 11-14, 16, 17 and 19 were not reexamined.

1. A medical balloon device, comprising a multiplicity of layers of thermoplastic film including layers sealed at peripheral edges thereof to form an inflatable interior volume enclosed by the sealed edges, *wherein the inflatable interior volume enclosed by the sealed edges is sealed by a single seal,* and layers *at least one of which is* sealed *directly to another* at one or more locations in the interior volume to enable the device to articulate to a predetermined shape upon inflation of the interior volume with an inflation fluid, to accommodate a predetermined medical application, wherein the inflatable interior volume is adapted to receive an inflation fluid.

\* \* \* \* \*